(12) United States Patent
Lewis

(10) Patent No.: US 8,480,680 B2
(45) Date of Patent: Jul. 9, 2013

(54) SPINAL DECOMPRESSION SYSTEM AND METHOD

(76) Inventor: Adam Lewis, Jackson, MS (US)

( * ) Notice: Subject to any disclaimer, the term of this patent is extended or adjusted under 35 U.S.C. 154(b) by 925 days.

(21) Appl. No.: 12/328,813

(22) Filed: Dec. 5, 2008

(65) Prior Publication Data

US 2009/0209965 A1 Aug. 20, 2009

Related U.S. Application Data

(60) Provisional application No. 61/012,138, filed on Dec. 7, 2007.

(51) Int. Cl.
*A61B 17/60* (2006.01)
(52) U.S. Cl.
USPC .............................. 606/90; 606/276; 606/248

(58) Field of Classification Search
USPC .................. 606/90, 248–249, 246, 247, 276, 606/277; 623/17.11, 17.15, 17.16
See application file for complete search history.

(56) References Cited

U.S. PATENT DOCUMENTS

| | | | | |
|---|---|---|---|---|
| 4,404,967 | A * | 9/1983 | Bacal et al. | 606/276 |
| 4,931,055 | A * | 6/1990 | Bumpus et al. | 606/60 |
| 5,910,171 | A * | 6/1999 | Kummer et al. | 623/18.11 |
| 8,048,118 | B2 * | 11/2011 | Lim et al. | 606/249 |
| 2005/0240182 | A1 * | 10/2005 | Zucherman et al. | 606/61 |
| 2006/0004447 | A1 * | 1/2006 | Mastrorio et al. | 623/17.11 |

* cited by examiner

*Primary Examiner* — David Isabella
*Assistant Examiner* — Marcia Hoffman
(74) *Attorney, Agent, or Firm* — Cermak Nakajima LLP; Adam J. Cermak

(57) ABSTRACT

A device useful for spinous process decompression includes a pair of prongs which can be moved apart from each other by rotation of a gear which mates with a threaded rod.

13 Claims, 8 Drawing Sheets

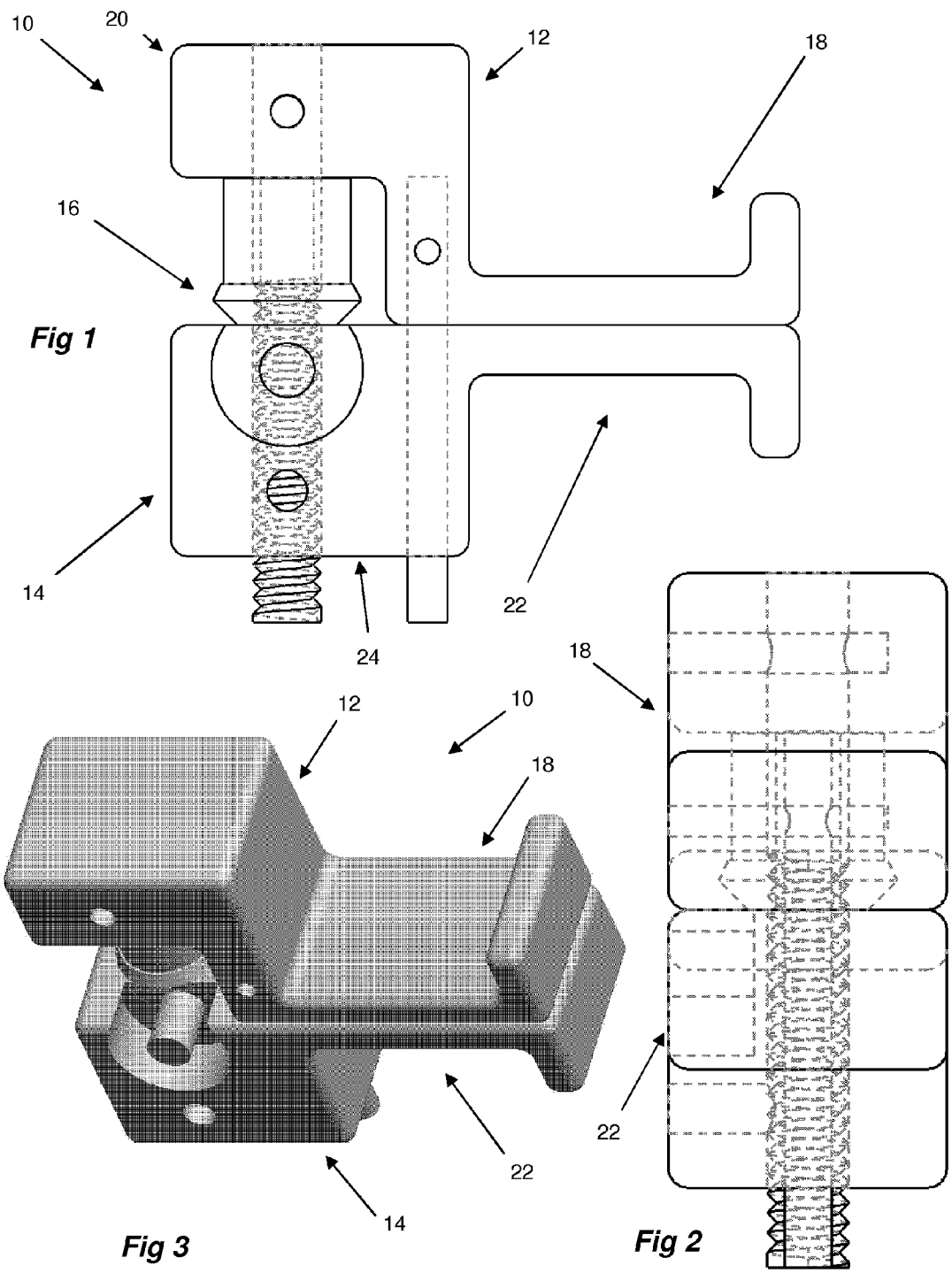

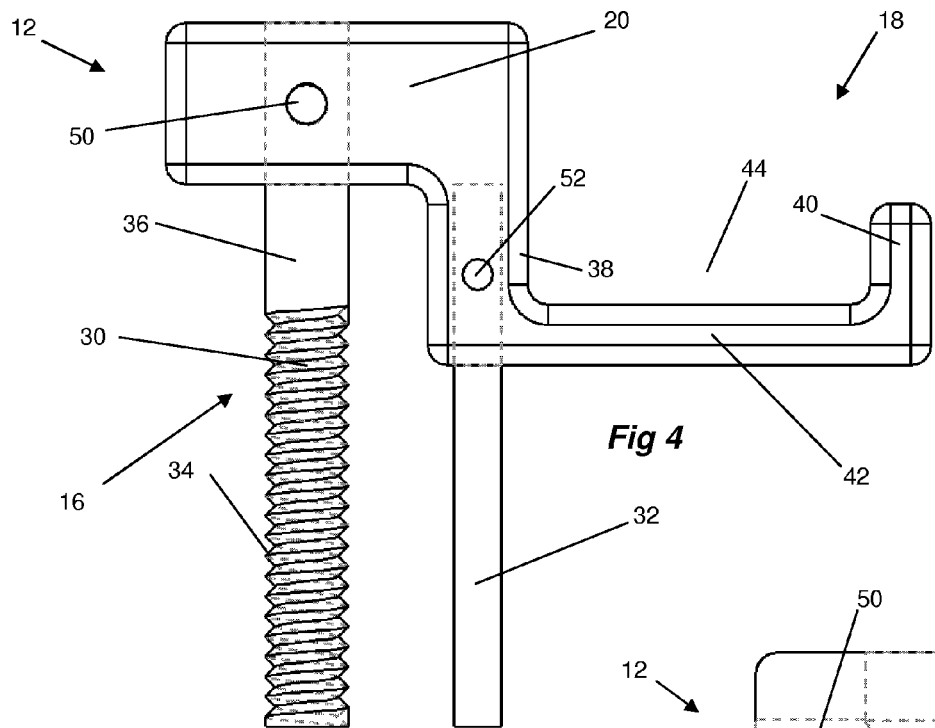
*Fig 4*
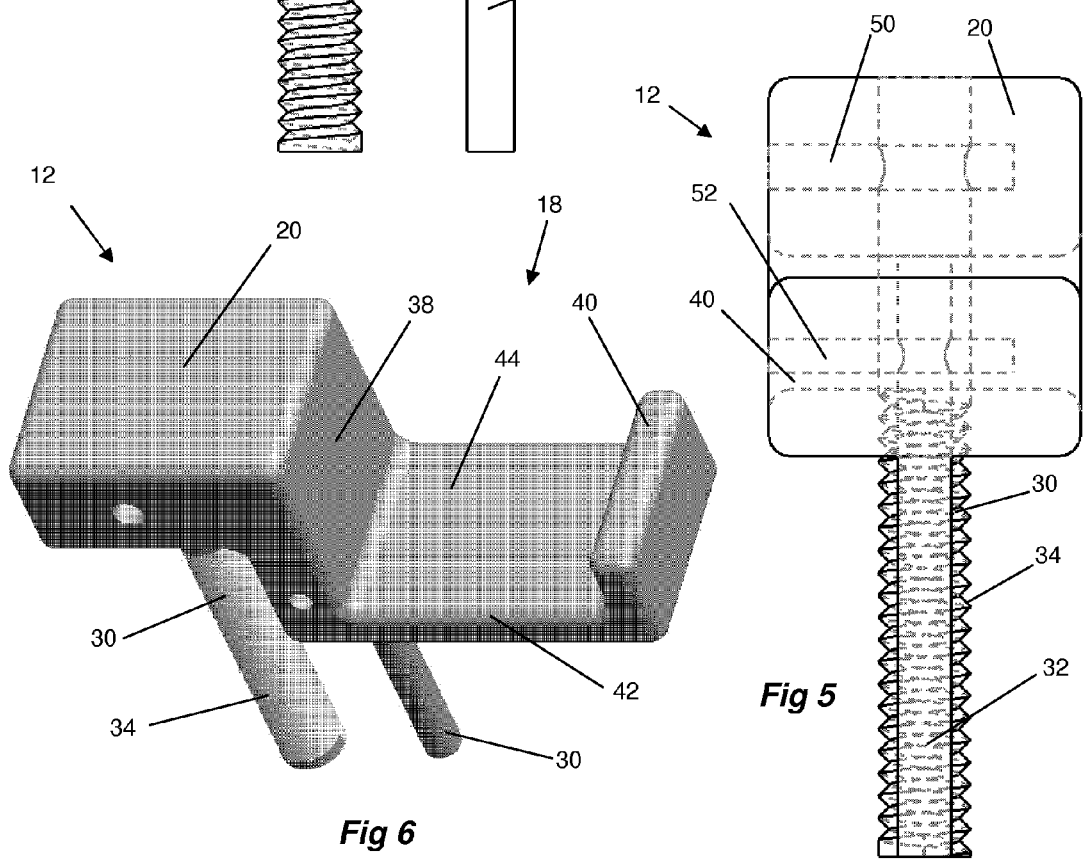
*Fig 6*
*Fig 5*

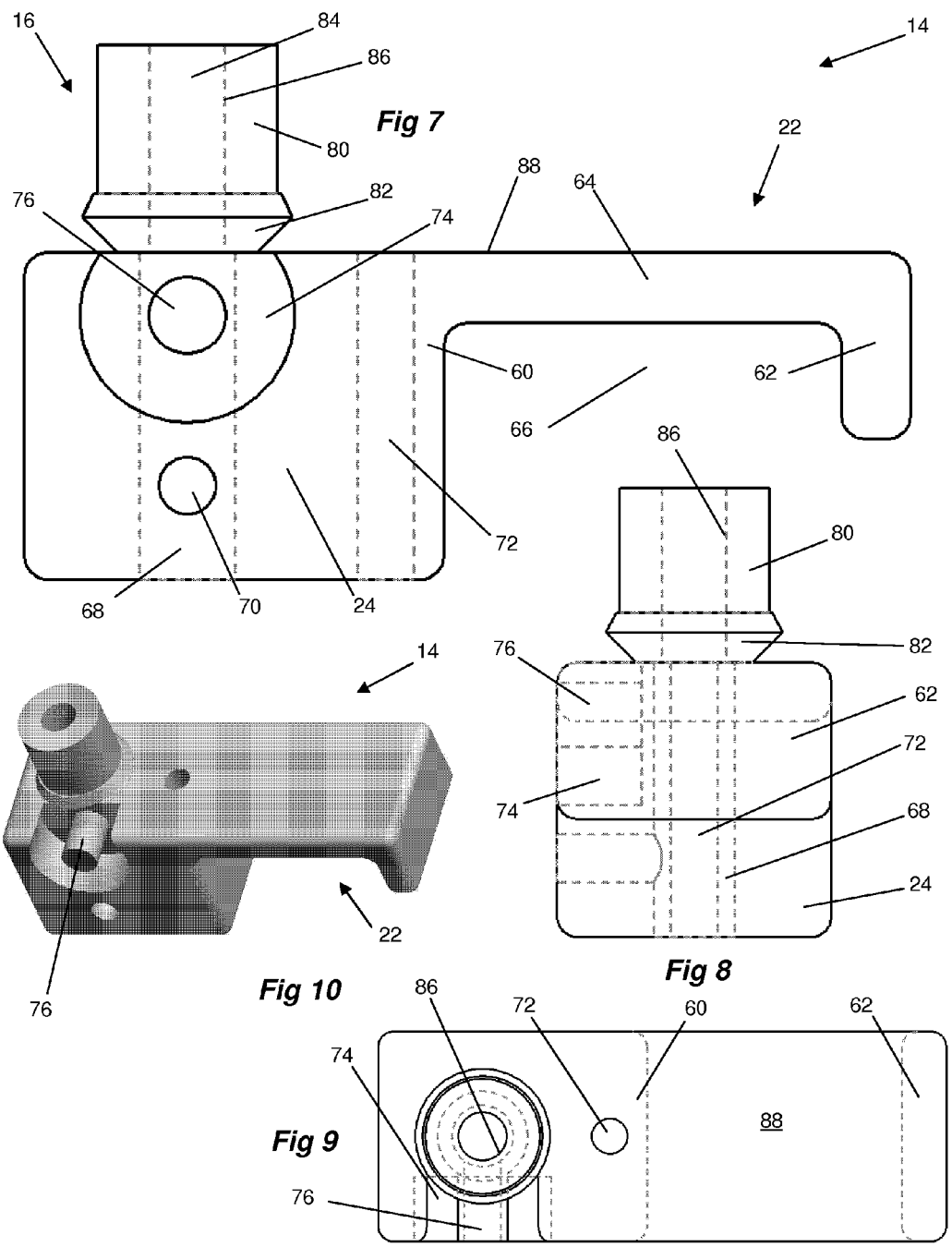

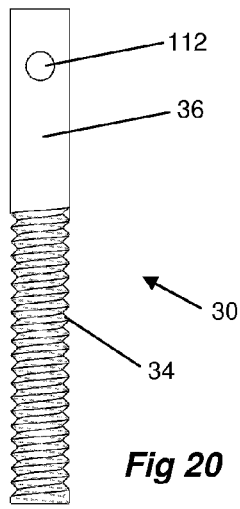
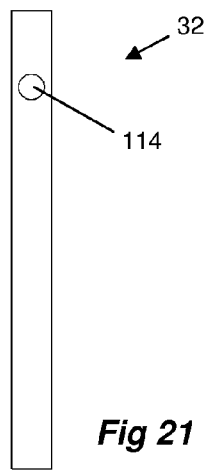
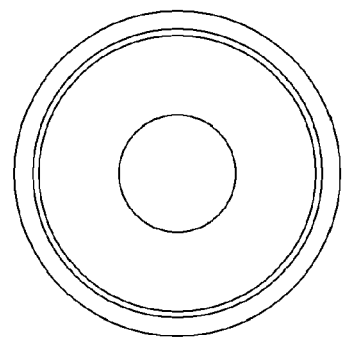
Fig 20  Fig 21  Fig 23
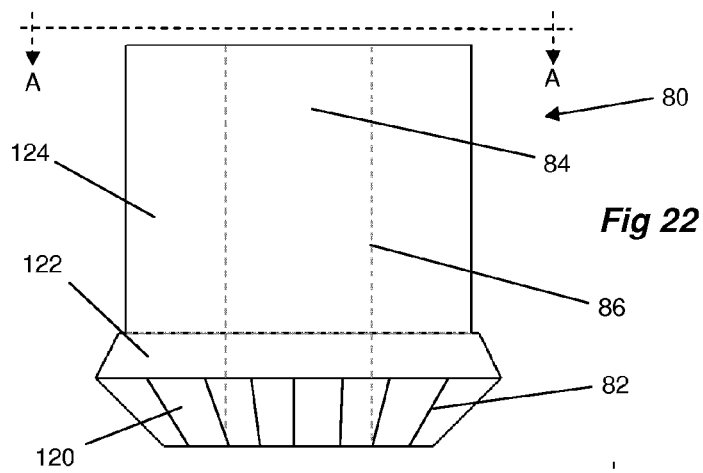
Fig 22
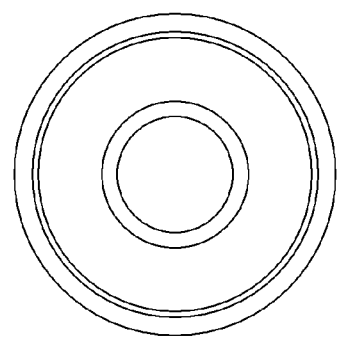
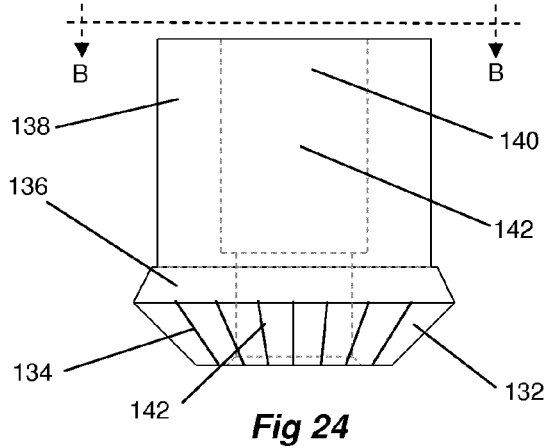
Fig 25  Fig 24

1

SPINAL DECOMPRESSION SYSTEM AND METHOD

This application claims priority under 35 U.S.C. §119 to U.S. provisional application No. 61/012,138, filed 7 Dec. 2007, the entirety of which is incorporated by reference herein.

BACKGROUND

1. Field of Endeavor

The present invention relates to devices, systems, and processes useful for spinal decompression.

2. Brief Description of the Related Art

Spinal decompression is currently used to treat neurogenic intermittent claudication secondary to a confirmed diagnosis of lumbar spinal stenosis, by removing part of the lamina and spinous process and placing screws and rods in the pedicles. The currently available devices and procedures require significant surgical intervention and long healing time for patients. Therefore, there remains a need for less invasive device and procedures, which can lead to less patient discomfort and shorter healing times.

SUMMARY

According to a first aspect of the invention, a spinal decompression system comprises a first portion including a first laterally extending prong, a second portion including a second laterally extending prong and a vertical throughbore, and a force transmission device connecting the first and second portions, the force transmission device including a first member attached to the first portion and extending through the bore in the second portion, and a second member engaging the first member and configured and arranged to linearly move the first member in the vertical throughbore.

According to another aspect of the present invention, a method of decompressing a portion of the spine of a patient, the portion of the spine including two anatomical structures, comprises inserting at least a part of a decompression device between said two anatomical structures, said decompression device including at two separable portions, each of the two separable portions bearing against one of said two anatomical structures, and mechanically moving the two separable portions apart from one another, the two separable portions pushing said two anatomical structures apart.

Still other aspects, features, and attendant advantages of the present invention will become apparent to those skilled in the art from a reading of the following detailed description of embodiments constructed in accordance therewith, taken in conjunction with the accompanying drawings.

BRIEF DESCRIPTION OF THE DRAWINGS

The inventions of the present application will now be described in more detail with reference to exemplary embodiments of the apparatus and method, given only by way of example, and with reference to the accompanying drawings, in which:

FIG. 1 illustrates a front side elevational view of an exemplary decompression device embodying principles of the present invention;

FIG. 2 illustrates a right side elevational view of the device of FIG. 1;

FIG. 3 illustrates a top, front, right perspective view of the device of FIG. 1;

FIG. 4 illustrates a front side elevational view of the upper prong of the device of FIG. 1;

FIG. 5 illustrates a right side elevational view of the upper prong of FIG. 4;

FIG. 6 illustrates a top, front, right perspective view of the upper prong of FIG. 4;

FIG. 7 illustrates a front side elevational view of the lower prong of the device of FIG. 1;

FIG. 8 illustrates a right side elevational view of the lower prong of FIG. 7;

FIG. 9 illustrates a top plan view of the lower prong of FIG. 7;

FIG. 10 illustrates a top, front, right perspective view of the lower prong of FIG. 7;

FIG. 20 illustrates front elevational view of a threaded rod portion of the upper prong of FIG. 4;

FIG. 21 illustrates front elevational view of a guide rod portion of the upper prong of FIG. 4;

FIG. 22 illustrates a front elevational view of a lip driven bevel gear portion of the lower prong of FIG. 7;

FIG. 23 illustrates a top plan view of the bevel gear portion of FIG. 22;

FIG. 24 illustrates a front elevational view of a lip driver bevel gear portion of an exemplary torque transmission element embodying principles of the present invention;

FIG. 25 illustrates a top plan view of the gear portion illustrated in FIG. 24;

DETAILED DESCRIPTION OF EXEMPLARY EMBODIMENTS

Figure 11:
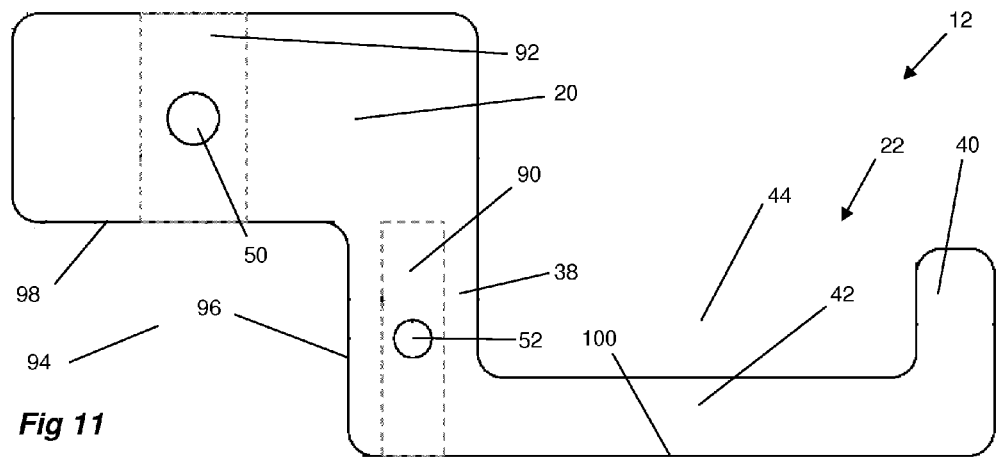
FIG. 11 illustrates a front elevational view of a portion of the top prong of FIG. 4.
Figure 12:
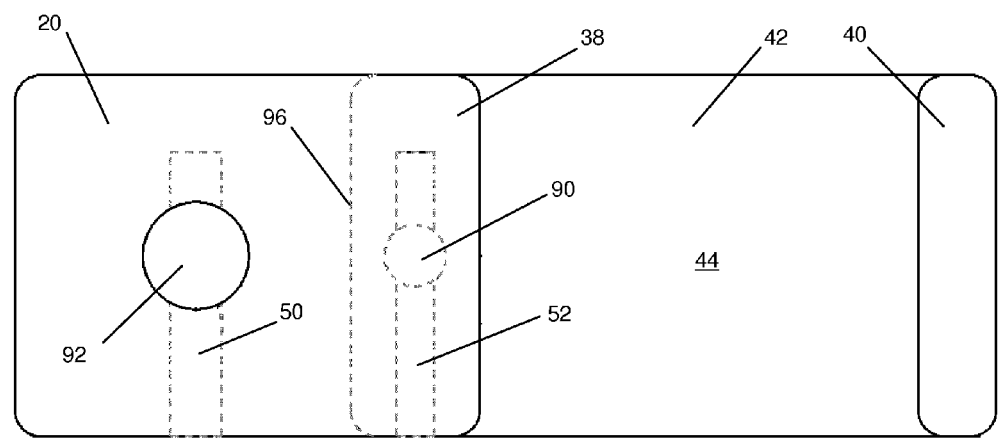
FIG. 12 illustrates a top plan view of the portion illustrated in FIG. 11.
Figure 13:
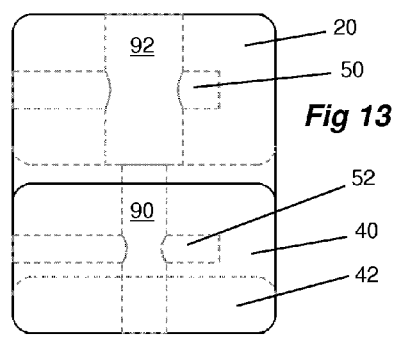
FIG. 13 illustrates a right side elevational view of the portion illustrated in FIG. 11.
Figure 14:
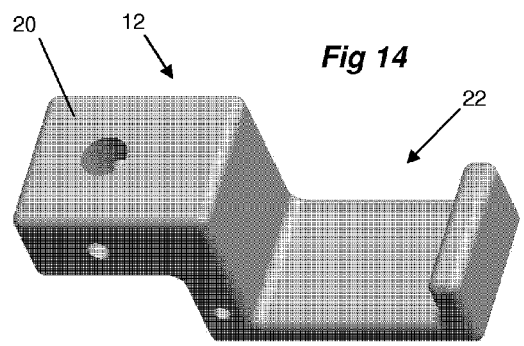
FIG. 14 illustrates a top, front, right perspective view of the portion illustrated in FIG. 11.

Referring to the drawing figures, like reference numerals designate identical or corresponding elements throughout the several figures.

In general terms, devices and processes embodying principles of the present invention aim to treat patients suffering from neurogenic intermittent claudication secondary to a confirmed diagnosis of lumbar spinal stenosis. Interspinous Process decompression devices and methods in accordance with the present invention are advantageously used for treating patients suffering from neurogenic intermittent claudication secondary to a confirmed diagnosis of lumbar spinal stenosis, e.g., for patients with moderately impaired physical function who experience relief in flexion from their symptoms of leg/buttock/groin pain, with or without back pain, and have undergone a regimen of extended, e.g., at least 6 months, of nonoperative treatment.

An exemplary implant in accordance with the present invention fits between the spinous process of the spine, and includes a single device which is distracted by using a torque transmission tool or screwdriver to rotate a cap portion of the device, which forces prongs of the implant to spread open. This causes and allows the spinous processes to spread apart and, in turn, decompresses the nerve roots. The implant can be made from any one or more of titanium, stainless steel, peek, ceramic, or any other material which has sufficient bioacceptability and material strength to function as a spinal implant as described herein.

In further general terms, the device includes three major components: a pair of opposed prongs which are moved towards and away from each other; and a force transmission device which includes a threaded rod and a bevel gear, in which rotation of the bevel gear is transmitted to the threaded rod and causes it to move linearly up and down. The rod is connected to one of the prongs, and a torque driver which mates with the bevel gear is used by the surgeon to turn the bevel gear, thus separating the prongs. When implanted as described elsewhere herein, exemplary devices thus permit a surgeon to selectively decompress the spinous processes.

Turning now to the drawing figures, a first exemplary embodiment of a spinal decompression device 10 is illustrated in FIGS. 1-3. The device 10 includes a first portion 12, an opposing second portion 14, and a force transmission device 16 which operates between the first and second portions. The first portion 12 generally includes a first prong 18 and a connector 20 which connects the prong to the force transmission device 16; similarly, the second portion 14 generally includes a second prong 22 and a connector 24 which connects the second prong to the force transmission device. Other details of these elements of this first exemplary embodiment are described in detail below.

With reference to FIGS. 4-6, the first portion 12 and portions of the force transmission device 16 are illustrated. The force transmission device 16 includes a threaded rod 30 having threads 34 on an external surface of the rod, and optionally includes a portion 36 which does not include threads. The rod 30 extends from the connector 20 in the direction of the second portion 14 of the device 10, as generally illustrated in FIG. 1. The rod 30 can be formed integrally with the connector 20, but is preferably a separate subcomponent. For this purpose, the connector 20 can include a bore 50 (which may be blind) into which a pin, set screw, or the like (not illustrated) can be inserted in order to secure the rod 30 to the connector. A guide rod 32 is optionally provided, extends parallel to the rod 30, and is part of or fixedly mounted to the connector 20 or the prong 18. Similarly, a bore 52 (which may be blind) can optionally be provided to receive a pin, set screw, or the like (not illustrated) to secure the guide pin in place.

The prong 18 extends laterally away from the connector 20, and is sized and configured to be able to decompress the spinous processes with the prong 22. According to this exemplary embodiment, the prongs 18 and 22 are similarly constructed, although other embodiments are not so restricted. The prong 18 preferably includes an upwardly extending first leg 38, an upwardly extending second leg 40, and a cross-member 42 which laterally connects the first and second legs. The two legs 38, 40 and the cross-member 42 together form a U-shape and thus delimit a channel 44 between the legs, in which portions of a patient's spinal can be received for decompression. While the distance between the legs 38, 40, and thus the length of the cross-member 42, is illustrated to be several times the height of the second leg 40, other exemplary embodiments are not so limited and other relative sizes of the subcomponents of the prong 18 can be used.

FIGS. 7-10 illustrate an exemplary second portion 14 and portions of an exemplary force transmission device 16. The second portion 14 includes the second prong 22 and a connector 24 which connects the second prong to portions of the force transmission device 16. The prong 22 extends laterally away from the connector 24, and is sized and configured to be able to decompress the spinous processes with the prong 18. The second prong 22 includes a downwardly extending first leg 60, a downwardly extending second leg 62 laterally spaced from the first leg, and a laterally extending cross-member 64 which connects the first leg to the second leg. The two legs 60, 62 and the cross-member 64 together delimit a channel 66 between the legs, in which portions of a patient's spinal can be received for decompression. While the distance between the legs 60, 62, and thus the length of the cross-member 64, is illustrated to be several times the height of the second leg 62, other exemplary embodiments are not so limited and other relative sizes of the subcomponents of the prong 22 can be used. Furthermore, while it is preferable that the first prong 18 and the second prong 22 are substantially mirror images of each other, other exemplary embodiments are not so restricted and the prongs can take on different forms.

The connector 24 includes a bore 68, which is preferably a throughbore, which extends vertically through the connector. The bore 68 is sized to slidingly receive the threaded rod 30, as described in greater detail below. A laterally extending blind bore 70 is optionally formed in the lower portions of the connector 24 and extends into the bore 68, and is sized to receive an optional pin, set screw, or the like (not illustrated) to set the vertical position of the threaded rod 30 relative to the connector 24, and therefore the distance between the first and second portions 12, 14. A second vertically extending bore 72 is also provided in the connector 24, and is sized and positioned to slidingly receive the guide rod 32 therein, when the first and second portions 12, 14 are mounted together.

A recess 74 is formed in a front face of the connector 24, and a cylindrical post 76 is located in the recess, advantageously centered, and extends laterally outwardly. The recess 74 is advantageously formed as a portion of an annulus with the recess opening up on its upper end to the upper surface 88 of the second portion 14. The recess 74 is provided to have a space in the second portion 14 in which the driving head of a torque transmission tool can be placed so that the head mates with portions of the torque transmission device 16, described below. As such, the recess is optional, when access to the torque transmission device 16 can be made in other manners. The post 76 is optionally provided to mate with a correspondingly sized recess in a torque driver tool, an example of which is described elsewhere herein, to assist in aligning and steadying the tool with respect to the second portion 14.

FIGS. 7-10 also illustrate a portion of the torque transmission device 16 resting on the top surface 88 of the second portion 14, in this exemplary embodiment the portion being a bevel gear 80. The gear 80 includes bevel gear teeth 82 on a surface of the gear 80 which is directed toward the recess 74, so that correspondingly configured gear teeth on a torque driver can mate with the teeth 82. The gear 80 also includes throughbore 84 which is internally threaded with screw threads 86 which are configured to mate with the threads 34 on the threaded rod 30. As can be more easily appreciated from FIG. 1, when the torque transmission device 16 is assembled, the threaded rod 30 extends through the bore 84 of the bevel gear 80 and through the bore 68 of the second portion 14, with the external threads 34 of the rod 30 mating with the internal threads 86 of the bore 84. In this manner, rotation of the bevel gear 80 is translated into upward or downward motion of the rod 30, which slides freely in bore 68, while the bevel gear 80 is not free to move up and down with the rod 30 because the threads 34, 86, mate. A coil spring (not illustrated) may optionally be provided between the bevel gear 80 and the connector 20, preferably around the rod 30, to additionally urge the bevel gear 80 downwardly and toward the recess 74.

FIGS. 11-14 are similar to FIGS. 4-6, but FIGS. 11-14 illustrate the first portion 12 without portions of the torque transmission device 16; accordingly, only additional features will be discussed. The connector 20 preferably includes bores 90, 92, to receive the rods 32, 30, respectively, when those rods are formed separate from the connector and are mounted therein. Bores 90, 92 can be either plain, threaded, or include other attachment structures, with the rods 32, 30 including corresponding structures. The connector 20 also includes a recess 94 adjacent to the first leg 38, delimited by sidewalls 96, 98, in which portions of the torque transmission device 16 are received. The connector 20 can include additional sidewalls to delimit the recess 94, for example, on the front, rear, and left ends of the connector 20, for any reason, e.g., to further enclose the bevel gear 80.

Figure 15:
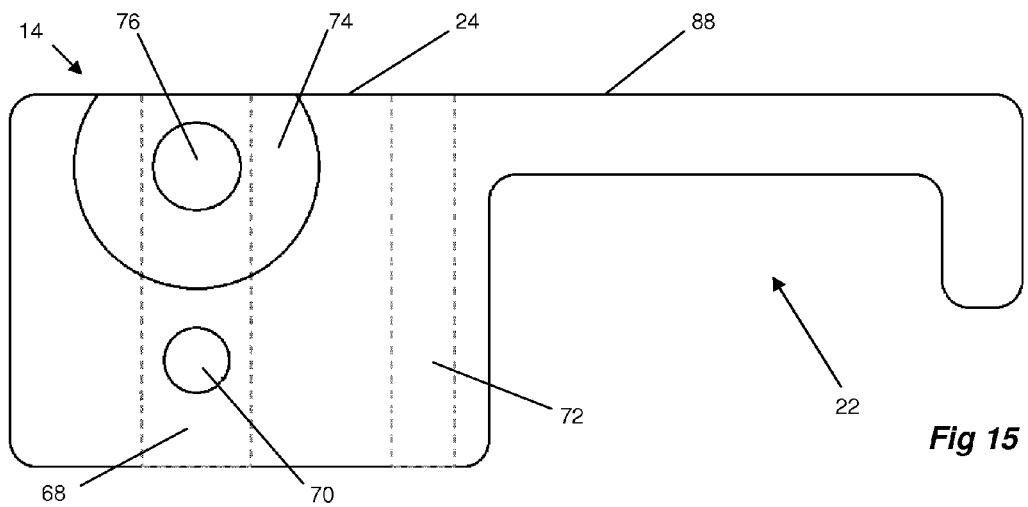
FIG. 15 illustrates a front elevational view of a portion of the lower prong illustrated in FIG. 7.
Figure 16:
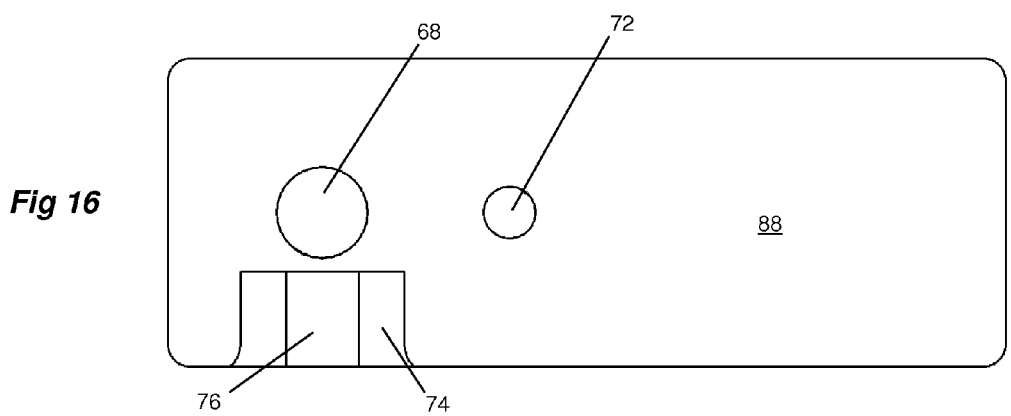
FIG. 16 illustrates a top plan view of the portion illustrated in FIG. 15.
Figure 17:
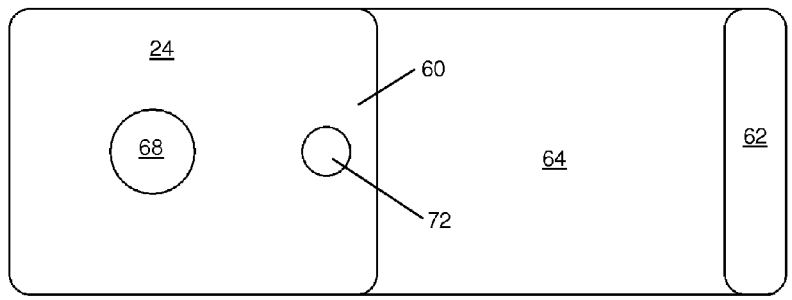
FIG. 17 illustrates a bottom plan view of the portion illustrated in FIG. 15.
Figure 18:
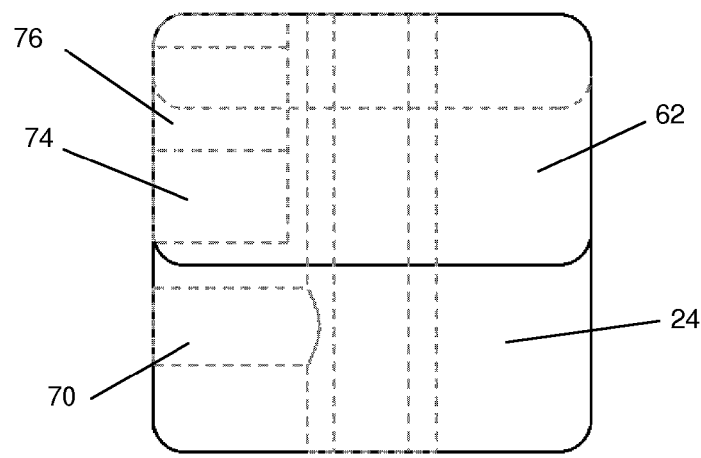
FIG. 18 illustrates a right side elevational view of the portion illustrated in FIG. 15.
Figure 19:
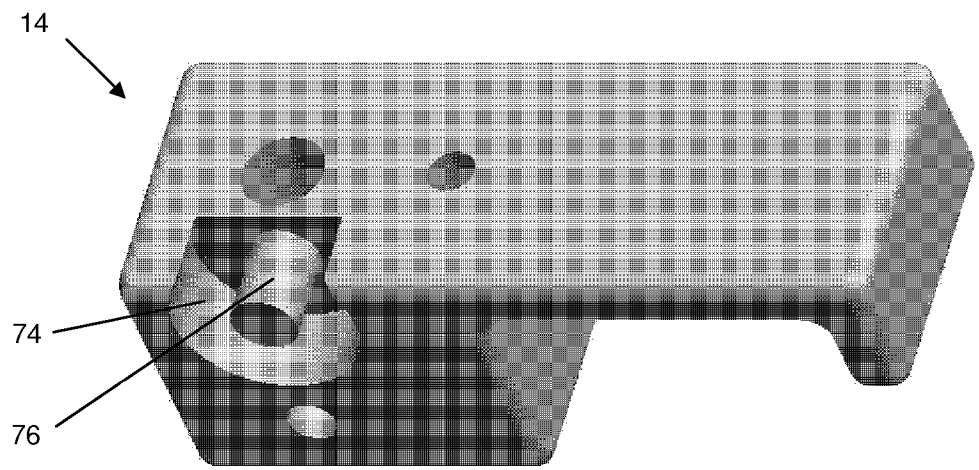
FIG. 19 illustrates a front, right perspective view of the portion illustrated in FIG. 15.

FIGS. 15-19 are similar to FIGS. 7-10, but FIGS. 15-17 illustrate the second portion 14 without portions of the torque transmission device 16; accordingly, only additional features will be discussed. In addition to the features already described, the second portion 14 includes an upper surface 88 which meets the lower surface 100 (FIG. 11) of the first portion 12, when the first and second portions are in the orientation illustrated in FIG. 1.

FIG. 20 illustrates the threaded rod 30, including the threads 34 and the optional unthreaded portion 36. Additionally, the rod 30 can optionally include a throughhole 112 configured and positioned to align with the bore 50, to receive a set screw or the like.

FIG. 21 illustrates the guide rod 32 which, similar to the rod 30, can optionally include a throughhole 114 configured and positioned to align with the bore 52, to receive a set screw or the like. FIGS. 22 and 23 illustrate the exemplary bevel gear 80 described elsewhere herein. In addition to the features already described, the gear 80 includes a first frustoconical section 120, on which the bevel gear teeth 82 are formed, a second, optional frustoconical section 122, oriented opposite to the first section 120, and a body 124 which can be cylindrical. FIG. 23 is a top plan view taken at line A-A in FIG. 22.

FIGS. 24 and 25 illustrate an exemplary bevel gear head 130 of a torque transmission driving tool that is advantageously used with the torque transmission device 16. The head 130 includes a first frustoconical section 134 on which bevel gear teeth 132 are formed, the teeth 132 configured to mate with the teeth 82, as mentioned elsewhere herein. The head 130 includes a second, optional frustoconical section 136, oriented opposite to the first section 134, and a body 138 which can be cylindrical. A throughbore 140 extends through the head 130, and includes an optional portion 142 sized and configured to receive the post 76 therein, when the head 130 is inserted into the recess 74 of the second portion 14. The bore 140 also includes a portion 142 configured to received a torque transmission rod, bit, or the like, as are well known to those of ordinary skill in the art. FIG. 25 is a top plan view taken at line B-B in FIG. 22.

Figure 26:
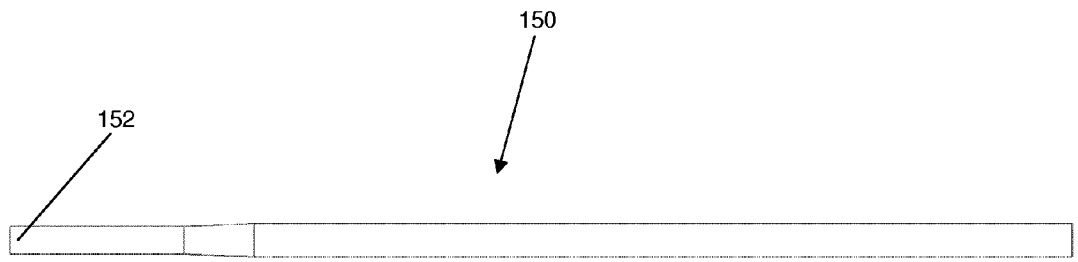
FIG. 26 illustrates a side elevational view of a torque transmission shaft portion of an exemplary torque transmission element embodying principles of the present invention.
Figure 27:
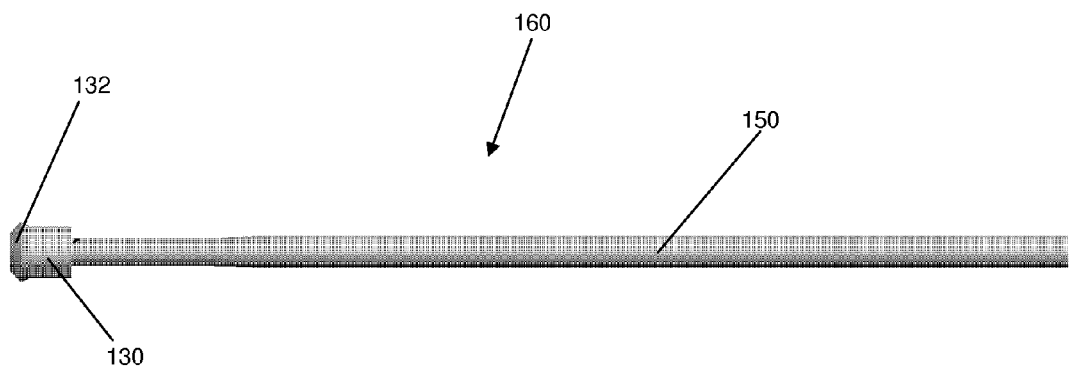
FIG. 27 illustrates a side elevational view of an exemplary torque transmission element embodying principles of the present invention, including the bevel gear and shaft of FIGS. 25 and 26 assembled together.

FIGS. 26 and 27 illustrate an exemplary drive tool 160 embodying principles of the present invention, including the exemplary head 130. A drive rod 150 includes a tip 152 sized to be received in the bore 142 and secured therein, e.g., by welding.

Operation of the exemplary device 10 will now be described with reference to the drawing figures. When spinal decompression is desire, the surgeon removes part of the lamina and accesses the spinous processes of interest. A decompression device embodying principles of the present invention, e.g, device 10, is inserted in place, with the device preferably in the orientation illustrated in FIG. 1, with the prongs 18, 22 positioned to push apart the anatomical structures that the surgeon wants to separate, e.g., the spinous processes of a patient whose spinous processes are abnormally close together. The surgeon inserts a driver, e.g., the head 130, against the bevel gear 80, and more particularly against the bevel gear teeth 82; when the second portion 14 includes the recess 74, the head 130 is inserted into the recess; and when the second portion 14 includes the post 76, the head 130 is inserted over the post. The bevel gear teeth of the bevel gear 80 and the head 130 mesh together, and the head is turned, either by spinning the rod 150, if connected to the head 130, or by activating a electrical motor fitted with a bit that transmits torque to the head 130. Rotation of the head 130 causes rotation of the gear 80, which in turn causes up or down linear motion of the threaded rod 30, by virtue of the mating of the threads 34, 84. Because the rod 30 is secured to the first portion 12, the linear movement of the rod 30 causes the first portion and the second portion to move apart (or towards each other, for rotation of the gear 80 in the opposite direction), while the guide rod 32 prevents the first and second portions from rotating relative to each other. If provided, the optional spring (not illustrated) maintains the bevel gear 80 against the top surface 88 of the second portion 14. Thus, the prongs 18, 22 force apart the anatomical structures between which they were inserted. When the desired separation of those anatomical structures is achieved, the surgeon can optionally, yet advantageously, fix the relative positions of the first and second portions 12, 14 by insertion of a set screw (not illustrated) or the like into bore 70 to bear against and lock in place the rod 30 relative to the second portion 14.

Systems and processes embodying principles of the present invention are not limited to the foregoing exemplary embodiments. By way of non-limiting example, cooperating elements can be reversed, e.g., the threaded rod 30 and the bevel gear 80 can be mounted to the other of the first and second portions; the bevel gear could include external threads, to mate with an internally threaded sleeve which would take the place of the threaded rod; the recess 74 can be on other faces of connector 24, in particular the left side face and/or rear face of the connector; and the like. Further alternatively, the torque transmission device 16, while preferable, can be replaced with another mechanism by which the first and second portions 12, 14 are mechanically separated. By way of a further non-limiting example, the device 16 could be replaced with a ratchet-and-pawl-type jack mechanism, a toothed rack replacing the threaded rod 30 and a ratchet-and-pawl replacing the bevel gear 80, and actuation of the jack being had by the typical rectilinear motion for such jacks.

While the invention has been described in detail with reference to exemplary embodiments thereof, it will be apparent to one skilled in the art that various changes can be made, and equivalents employed, without departing from the scope of the invention. The foregoing description of the preferred embodiments of the invention has been presented for purposes of illustration and description. It is not intended to be exhaustive or to limit the invention to the precise form disclosed, and modifications and variations are possible in light of the above teachings or may be acquired from practice of the invention. The embodiments were chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

What is claimed is:

1. A spinal decompression system comprising:
    a first portion including a first laterally extending prong;
    a second portion including a second laterally extending prong and a vertical throughbore; and
    a force transmission device connecting the first and second portions, the force transmission device including
        a first member attached to the first portion and extending through the bore in the second portion, and
        a second member engaging the first member and configured and arranged to linearly move the first member in the vertical throughbore;
    wherein the second portion includes a second connector that extends laterally from the second prong, the second member being positioned adjacent to the second connector and extending vertically away therefrom; and
    wherein the second connector includes a vertical guide bore, the first portion further comprises a vertically extending guide rod slidably positioned in the guide bore, and the vertical guide bore and the vertically extending guide rod are positioned laterally between the first and second laterally extending prongs and the force transmission member.

2. A system according to claim 1, wherein the first portion includes a first connector that extends laterally from the first prong, the first member being attached to the first connector and extending vertically away therefrom.

3. A system according to claim 2, wherein the first connector includes a recess, and the second member is positioned in the recess.

4. A system according to claim 1, wherein the first member comprises a threaded rod.

5. A system according to claim 1, wherein the second connector includes a laterally extending recess adjacent to the second member.

6. A system according to claim 5, wherein the recess consists essentially of a portion of an annulus.

7. A system according to claim 6, wherein the second connector comprises a laterally extending cylindrical post in the center of said portion of said annulus.

8. A system according to claim 1, wherein the second member comprises a bevel gear having external bevel gear teeth oriented towards the second portion, a vertically extending bore, and internal threads on said vertically extending bore.

9. A system according to claim 8, wherein the first member comprises a threaded rod positioned in the vertically extending bore of the bevel gear, with the bevel gear internal threads mating with the threaded rod external threads.

10. A system according to claim 1, further comprising:
    a drive head configured and arranged to mate with the second member to cause the second member to move the first member.

11. A system according to claim 10, wherein the drive head comprises a bevel gear and the second member comprises a bevel gear.

12. A system according to claim 1, wherein at least one of the first and second prongs comprises:
    a vertically extending first leg;
    a vertically extending second leg spaced from the first leg; and
    a laterally extending cross-member joining the first and second legs;
    wherein the first leg, the second leg, and the cross-member together form a U-shape and delineate a channel therebetween for receiving a portion of the spinal anatomy.

13. A method of decompressing a portion of the spine of a patient, the portion of the spine including two anatomical structures, the method comprising:
    inserting at least a part of a spinal decompression system according to claim 1 between said two anatomical structures, each of the first and second portions bearing against one of said two anatomical structures; and
    mechanically moving the first and second portions apart from one another, the first and second portions pushing said two anatomical structures apart.

* * * * *